United States Patent [19]

Green

[11] Patent Number: 4,832,946

[45] Date of Patent: May 23, 1989

[54] COSMETIC COMPOSITION

[76] Inventor: Martin R. Green, Yew Tree Cottage, Water Stratford Buckingham, United Kingdom, MK18 5DU

[21] Appl. No.: 132,821

[22] Filed: Dec. 14, 1987

[30] Foreign Application Priority Data

Dec. 23, 1986 [GB] United Kingdom ............. 8630720

[51] Int. Cl.$^4$ .................... A61K 7/06; A61K 37/02
[52] U.S. Cl. ...................... 424/70; 424/115; 514/21; 514/880; 435/948
[58] Field of Search ............ 424/70, 95, 115, 116; 514/1, 2, 21, 880; 530/350, 399, 842; 435/68, 240.2, 948

[56] References Cited

U.S. PATENT DOCUMENTS 4,139,619  2/1979  Chidsey .
4,761,401  8/1988  Couchman et al. ............ 514/844 X

FOREIGN PATENT DOCUMENTS 0064012  4/1982  European Pat. Off. .
0107885  5/1984  European Pat. Off. .
0213999  7/1986  European Pat. Off. .
236014   9/1987  European Pat. Off. .
3431266  8/1984  Fed. Rep. of Germany .
2395756  3/1979  France ........................... 424/70
2472385 12/1979  France .
8504577 10/1985  PCT Int'l Appl. .
8604231  7/1986  PCT Int'l Appl. .

OTHER PUBLICATIONS

Messenger, A. G. British Journal of Dermatology 2/(1984) 110, 685–689.

Primary Examiner—Ellis P. Robinson
Assistant Examiner—Susan S. Rucker
Attorney, Agent, or Firm—Daniel S. Ortiz; Melvin H. Kurtz

[57] ABSTRACT

A composition suitable for topical application to mammalian skin or hair, comprises an amount of the cell-free supernatant from a culture of dermal papilla fibroblasts which is sufficient to increase hair growth in the rat, when applied thereto, by at least 10% more than that obtainable using a control composition from which the said cell-free supernatant has been omitted.

17 Claims, No Drawings

COSMETIC COMPOSITION

FIELD OF THE INVENTION

The invention relates to a cosmetic or pharmaceutical composition for topical application to mammalian skin, the composition containing a hair growth promoter which is capable of promoting terminal hair growth, especially on the human scalp.

BACKGROUND

The Hair Bulb

The hair bulb is a compact, elongate structure, located in the dermis, composed of three main cellular groups:

(i) a compact group of fibroblasts including a capillary system known as the dermal papilla;

(ii) surrounding epithelial tissue, a component of which proliferates and differentiates to give rise to the mature hair shaft, and (iii) a group of fibroblasts present around the outside of the bulb in the connective tissue sheath.

It is well recognised that the dermal papilla is essential for hair growth [Oliver R F (1970) J Embryol Exp Morphol 23, 219-236] and that, consequently, it is also essential for the proliferation of the adjacent epithelial cells which give rise to hair.

The Hair Growth Cycle

It should be explained that in most mammals, hair does not grow continuously, but undergoes a cycle of activity involving alternate periods of growth and rest. The hair growth cycle can be divided into three main stages, namely:

(i) the growth phase known as anagen, during which the hair follicle penetrates deep into the dermis with the cells of the bulb dividing rapidly and differentiating to form the hair, (ii) the transitional stage known as catagen, which is heralded by the cessation of mitosis, and during which the follicle regresses upwards through the dermis and hair growth ceases, (iii) the resting stage known as telogen, in which the regressed follicle contains a small secondary germ with an underlying ball of tightly packed dermal papilla cells.

The initiation of a new anagen phase is revealed by rapid proliferation of epithelial cells in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

PRIOR ART

Alleged Baldness Cures

Although there have been many claims in the scientific literature to the promotion or maintenance of hair growth, by the topical application of hair tonics and the like, with the possible exception of minoxidil, none has ever proved to be effective or to be sufficiently free from disadvantageous clinical side effects, whether administered topically, orally or systemically, to warrant commercial exploitation as an ethical pharmaceutical, proprietary medicine, or as a cosmetic product.

Possibly, the only means which has met with partial success for growing hair on the bald or balding human head is transplantation of hair to the bald areas. This is, however, a painful operation and is not always successful. Furthermore, it is immediately apparent to the casual observer that the subject has received a hair transplant and it may take many months or even years before hair regrowth, following this operation, assumes an appearance which resembles that of naturally growing hair.

Among the many hair regrowth studies that have been reported in the literature, there is included the work of Bazzano as described in PCT International Publication No. WO 85/04577. This publication describes a composition which is useful for increasing the rates of hair growth on mammalian skin, prolonging the anagen phase of the hair growth cycle and for treating various types of alopecias. The composition in question contains a pyrimidine carbamate.

It has also been reported in U.S. Pat. No. 4 139 619 to Chidsey assigned to the Upjohn Company, that a topical composition comprising minoxidil as the free base or acid addition salt thereof, or certain specified related iminopyrimidines, is useful in stimulating the conversion of vellus hair to growth as terminal hair, as well as increasing the rate of growth of terminal hair.

In spite of the apparent stimulation of hair growth or regrowth in a small percentage of patients reported independently by Bazzano and Chidsey, there is some concern that systemic side-effects can result, particularly following topical application of minoxidil. Thus it is generally recognised in the medical literature that the side effects of orally administered minoxidil are very serious, and include fluid retention, tachycardia, dyspnea, gynecomastia, fatigue, nausea and cardiotoxicity.

It has also been proposed in DE-A-3 431 266 (Birzer) to administer externally or internally hair bulb cells with the papilla from slaughtered animals in order to stimulate growth and genesis of hair and to counteract hair loss and hair greying. The cells are obtained from the hide of animals and can be applied internally by injection or as tablets or drops, and externally as shampoos, creams and soaps.

The isolation of dermal papillae from human hair follicles has been reported by Messenger, A.G., British Journal of Dermatology (1984), 110, 685–689. Messenger has established primary cell cultures from the papilla explants in a nutrient medium.

BACKGROUND TO THE INVENTION

Experience has shown that it is difficult to harvest a substantial quantity of dermal papilla cells, either by dissection or by the enzymic treatment of animal hides advocated by Birzer [supra]. Furthermore, it has been discovered that the dermal papilla cells obtained from animals are not effective in promoting hair growth in the human subject, and that ideally, human dermal papilla cells should be employed for this purpose. Accordingly, cells derived from one host (e.g. cow) are immunologically distinct from any other species (e.g. man,, and therefore, it is not surprising that upon injection, they are rejected by the new host's immune system and destroyed.

Of course, if it is desired to promote hair growth in other mammals using animal cells, then ideally dermal papilla cells derived from the corresponding species of mammal should be employed.

Having regard to the fact that man has sought ways and means for promoting hair growth or regrowth in the bald or balding human subject since time immemorial, without discovering a totally safe, feasible and satisfactory treatment for promoting hair growth, it is all the more surprising that a means has now been discovered for generating a hair growth promoter from mammalian dermal papilla cells.

Essentially, we have been able to isolate hair follicles from skin and culture dermal papilla cells derived therefrom in a nutrient medium to obtain enhanced numbers of cells. Culture supernatants, rich in hair growth promoter, have been harvested from cultured human dermal papilla cells, and after concentration, applied topically to bald or balding human scalps in order to promote hair growth or regrowth.

DEFINITION OF THE INVENTION

Accordingly, the invention provides a composition suitable for topical application to mammalian skin or hair, comprising an amount of the cell-free supernatant from a culture of dermal papilla fibroblasts which is sufficient to increase hair growth in the rat, when applied thereto, by at least 10% more than that obtainable using a control composition from which the said cell-free supernatant has been omitted.

More particularly, the invention provides a composition suitable for topical application to mammalian skin or hair comprising an amount of a hair growth promoter, or active fragments thereof, sufficient to increase hair growth, in the rat, when applied thereto, by at least 10% more than that obtainable using a control composition from which said hair growth promoter has been omitted; and a cosmetically acceptable vehicle; the hair growth promoter having been obtained from a cell-free supernatant of cultured dermal papilla fibroblasts, the hair growth promoter being proteinaceous, and being further characterised by:
(a) having an apparent molecular weight of at least 500D; and
(b) possessing the ability to initiate DNA synthesis in a culture of serum starved NIH 3T3 cells.

DISCLOSURE OF THE INVENTION

The Supernatant from Culture of Dermal Papilla Fibroblasts

The composition according to the invention comprises a cell-free supernatant obtained from the culture of dermal papilla fibroblasts in an amount which is sufficient to increase hair growth in the rat, when applied thereto, usually topically, by at least 10% more than that obtainable using a control composition from which said cell-free supernatant has been omitted.

Preferably, the cell-free culture supernatant is concentrated, for example by ultra filtration at least 50 times, most preferably at least 100 times.

The procedure for culture of dermal papilla fibroblasts and isolation of the culture supernatant and its concentration is described more fully later in this specification.

The cell-free supernatant has been shown to contain a proteinaceous hair growth promoter.

The Hair Growth Promoter

The composition according to the invention more particularly comprises a proteinaceous hair growth promoter which is further characterised by:
(a) having a molecular weight of at least 500D; and
(b) possessing the ability to initiate DNA synthesis in a culture of serum-starved NIH 3T3 cells, that is, resting cells maintained in a nutrient medium containing 0.5% by volume of serum.

DNA synthesis can be determined by measuring the uptake of tritiated thymidine by the method as hereinafter described.

The hair growth promoter can be obtained by culturing dermal papilla fibroblasts in nutrient medium followed by separation of the supernatant liquid from such cultures, centrifuging the supernatant to remove cells and cell debris, and concentrating and dialysing the supernatant to remove substances having an apparent molecular weight of <500D, preferably <2000D.

The cell free concentrate so obtained contains the hair growth promoter having an apparent molecular weight of at least 500D, preferably from 500D to 1,000,000D, which is then incorporated in the composition according to the invention together with a suitable vehicle. Alternatively, the cell free concentrate after dialysis can be dried, preferably by freeze drying prior to incorporation in the composition according to the invention.

Although the hair growth promoter generally has an apparent molecular weight of >500D, it is believed that certain fragments derived from the hair growth promoter can also show activity in promoting hair growth or regrowth.

According to a preferred embodiment of the invention, the cell-free dermal papilla fibroblast culture supernatant is concentrated about one hundred times to provide a concentrate, containing the hair growth promoter, having a protein level of not greater than 10mg/ml, usually from 2 to 3 mg/ml.

The amount of this hair growth promoter to be incorporated with a suitable vehicle into compositions for topical use can vary widely, but in general, an amount expressed as protein of from 0.00001 to 99%, preferably from 0.001 to 90% by weight of the composition will provide an adequate dose of the hair growth promoter to the skin following topical application.

The Vehicle

The composition according to the invention also comprises a solid, semi-solid or liquid cosmetically and-/or physiologically acceptable vehicle, to enable the hair growth factor substance to be conveyed to the skin at an appropriate dilution. The nature of the vehicle will depend upon the method chosen for topical administration of the composition. The vehicle can itself be inert or it can possess physiological or pharmaceutical benefits of its own.

The selection of a vehicle for this purpose present a wide range of possibilities depending on the required product form of the composition.. Suitable vehicles can be classified as described hereinafter.

It should be explained that vehicles are substances which can act as diluents, dispersants, or solvents for the hair growth promoter which therefore ensure that it can be applied to and distributed evenly over the hair and/or scalp at an appropriate concentration. The vehicle is preferably one which can aid penetration of the hair growth promoter into the skin to reach the immediate environment of the hair follicle. Compositions according to this invention can include water as a vehicle, and/or at least one cosmetically acceptable vehicle other than water, including the concentrated dialysed culture supernatant, which will normally be aqueous in nature, obtained by the concentration step referred to earlier in this specification.

Vehicles other than water that can be used in compositions according to the invention can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, ispropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polthylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carbocymethyl cellulose, ethylene glycol monostearate.

The amount of vehicle in the composition, including water if present, should preferably be sufficient to carry at least a portion of a selected hair growth factor substance to the skin in an amount which is which is sufficient effectively to enhance hair growth. The amount of the vehicle can comprise the balance of the composition, particularly where little or no other ingredients are present in the composition. Accordingly, the vehicle or vehicles can comprise from 1 to 99.9999%, preferably from 50 to 99.5% and ideally from 90 to 99% by weight of the compositions.

Perfume

The composition according to the invention can also optionally comprise a perfume in an amount sufficient to make the composition acceptable to the consumer and pleasant to use. Usually, the perfume will form from 0.01 to 10% by weight of the composition.

Activity Enhancer

The composition according to the invention can also optionally comprise an activity enhancer which can be chosen from a wide variety of molecules capable of functioning in different ways to enhance the benefit of the hair growth promoter. Particular classes of activity enhancers include other hair growth stimulants, protein stabilising agents and penetration enhancers, whose presence can further improve the delivery of the hair growth promoter through the stratum corneum to the immediate environment of the hair follicle.

(i) Other Hair Growth Stimulants

Examples of other substances which themselves possess the ability to stimulate or increase the rate of terminal hair growth include, for example;
Benzalkonium chloride
Benzethonium chloride
Phenol
Estradiol
Diphenhydramine hydrocholoride
Chlorpheniramine maleate
Chlorophyllin derivatives
Cholesterol
Salicylic acid
Cystine
Red pepper tincture
Benzyl nicotinate
dl-Menthol
Peppermint oil
Calcium pantothenate
Panthenol
Castor oil
Hinokitiol
Prednisolone
Resorcinol Further substances which themselves possess the ability to increase the rate of terminal hair growth include:

α-1,4 esterified disaccharides described by Choay S.A. in EP-A No. 0 064 012, having the structure:

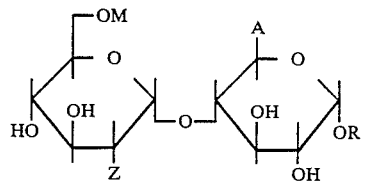

where
Z represents a functional nitrogen group, such as an azide or a group having the structure —NHB represents —H or a functional group such as acetyl or sulphate as a salt with an organic or mineral cation;

M represents —H or $SO_3M_1$, where $M_1$ is an organic or metallic cation, particularly an alkali metal; or an acetyl group;

R represents a $C_1$ to $C_4$ alkyl radical, especially methyl; or an aryl radical;

A represents a functional group such as an acid or —$COOR_1$, where $R_1$ represents —H or a $C_1$ to $C_4$ alkyl radical, especially methyl; or a metal, especially an alkali metal;

esterified oligosaccharides as described by Unilever in EP-A No. 0 211 610 including at least one esterified disaccharide unit consisting of a uronic acid residue having the structure:

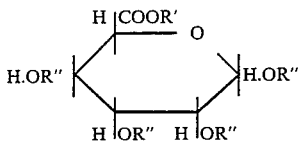

and a hexosamine residue having the structure:

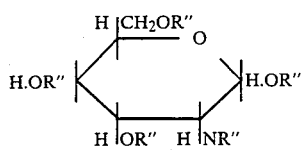

where
R' is $C_3$ to $C_{10}$ alkyl or

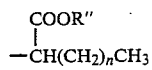

R" is —H, $C_1$ to $C_4$ al .
R'" is —H, —CO(CH$_2$)$_m$CH$_3$, or —SO$_3$M,
M is —H, or a metallic or organic cation
n is 0 or an integer of from 1 to 7, and
m is 0 or the integer 1 or 2;
the groups designated R" being the same or different, one R" group from each pyranose ring structure being linked by a glycosidic linkage having the configuration α-1,3, α-1,4, β-1,3 or β-1,4; and the —COOR', —CH$_2$OR" and —OR" groups being of either configuration with respect to the pyranose rings;

Minoxidil and its derivatives, as described by the Upjohn Co, in GB 1 167 735,

Minoxidil glucuronide, as described by Unilever in EP-0 242 967

Minoxidil sulphates, as described by the Upjohn Co., in WO 86/04231.

(ii) Protein Stabilising Agents

As has been stated earlier, the hair growth promoter is proteinaceous, and therefore its benefit in promoting hair growth can be maintained or improved by including a protein stabilising agent in the composition according to the invention. As an example of this effect, it is to be noted that the skin contains natural proteases which might at least partially degrade the hair growth promoter. Therefore, the presence of protein stabilising agent such as a protease inhibitor or a secondary protein for which with the hair growth promoter, the natural skin proteases will compete, can protect the hair growth promoter until it reaches the immediate environment of the hair bulb.

Examples of protein stabilising agent accordingly include:
Glycerol
Ethylemediaminetetraacetic acid
Cysteine
α$_2$-Macroglobulin
Serum, and
other proteinase inhibitors.

(iii) Penetration Enhancers

As has been stated earlier, the presence of a penetration enhancer can potentiate the benefit of the hair growth promoter by improving its delivery through the stratum corneum to its site of action in the immediate environment of the hair follicle close to the dermal papilla.

The penetration enhancer can accordingly function in a variety of ways. It can for example, improve the distribution of the hair growth promoter on the skin surface or, it can increase its partition into the skin from the composition when applied topically, so aiding its passage to its site of action. Other mechanisms enhancing the benefit of the hair growth promoter may also be involved.

Examples of penetration enhancers accordingly include certain non-electrolytes, such as:
2-methyl propan-2-ol
Propan-2-ol
Ethyl-2-hydroxypropanoate
Hexan-2,5-diol
POE(2) ethyl ether
Di(2-hydroxypropyl) ether
Pentan-2,4-diol
Acetone
POE(2) methyl ether
2-hydroxypropionic acid
Propan-1-ol
1,4 Dioxane
Tetrahydrofuran
Butan-1,4-diol Other penetration enhancers whose presence in the composition according to the invention can further improve the delivery through the stratum corneum include certain esters, such as:
Propylene glycol dipelargonate
Polyoxypropylene 15 stearyl ether
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibenzyl sebacate
Dibutyl suberate
Dioctyl azelate
Dibutyl azelate
Dimethyl azelate
Dibutyl succinate
Dibutyl phthalate
Didecyl phthalate
Ethyl myristate
Butyl myristate
Isopropyl palmitate
Ethyl laurate
Decyl oleate
2-ethyl-hexyl pelargonate
Isopropyl isostearate
Butyllaurate
Benzyl benzoate
Butyl benzoate
Hexyl laurate
Ethyl caprate
Ethyl caprylate
Ethyl caproate
Butyl stearate Benzyl salicylate, and
Ethyl salicylate Yet further penetration enhancers include esters of pyroglutamic acid having the structure:

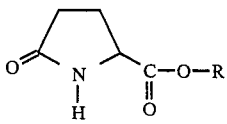 (1)

where R is $C_1$ to $C_{30}$ alkyl, or

and where R' and R" are the same or different and are each represented by H or the grouping:

$$[(CH_3)_u, (CH_2OH)_v, (CH_2)_w, (CH_3CH_2)_x, (CH_3CH_2)_x, (CH=CH)_z]- \quad (2)$$

where
u is zero or 1
v is zero, or the integer 1 or 2,
w is zero, or an integer of from 1 to 21
x is zero, or an integer of from 1 to 4,
y is zero, or the integer 1 or 2,
z is zero, or an integer of from 1 to 22, and
u+v+w+x+y+z is an integer of from 1 to provided that when the subgrouping (CH=CH) is present, then the total number of carbon atoms in said grouping is from 10 to 22.

Examples of suitable esters of pyroglutamic acid where R in structure (1) is $C_1$ to $C_{30}$ alkyl are:
pyroglutamic acid methyl ester
pyroglutamic acid ethyl ester
pyroglutamic acid n-propyl ester
pyroglutamic acid n-butyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid n-tridecyl ester
pyroglutamic acid n-tetradecyl ester
pyroglutamic acid n-hexadecyl ester
pyroglutamic acid n-octadecyl ester
pyroglutamic acid n-eicosyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2-hexyldecyl ester
pyroglutamic acid 2-octyldodecyl ester
pyroglutamic acid 2,4,4-trimetyl-1-pentane ester
pyroglutamic acid methyloctyl ester Particularly preferred esters of this group are those where R in structure (1) is $C_1$ to $C_{14}$ alkyl, (linear or branched), especially $C_1$ to $C_6$ (linear or branched).

Further examples of preferred esters of pyroglutamic acid, where R in structure (1) is

are those where R' and/or R" having the structure shown for grouping (2), include straight and branched chain, saturated or unsaturated aliphatic groups having from 1 to 2 carbon atoms, such as the alkyl groups:
methyl
ethyl
propyl
iso-propyl
butyl
iso-butyl
n-valeryl
iso-valeryl
n-caproyl
n-heptyl
n-caprylyl
n-capryl
lauryl
myristyl
palmityl
stearyl, and arachidyl.
and the $C_{10-22}$ alkenyl groups:
linoleyl
linolenyl
α-linolenyl
arachidonyl, and columbinyl.

Further examples of the grouping (2) also include hydroxyalkyl groups having from 1 to 22 carbon atoms, such as:
hydroxymethyl
2-hydroxyethyl
2-hydroxy-n-propyl
3-hydroxy-n-propyl
2-hydroxy-n-butyl
3-hydroxy-n-butyl
4-hydroxy-n-butyl
5-hydroxy-n-valeryl
6-hydroxy-n-caproyl
2,3-dihydroxy-n-propyl
2,3-dihydroxy-n-butyl
12-hydroxystearyl.

It is to be understood that the above list is not exhaustive, there being many other examples of alkyl or substituted alkyl groups expressed by the above generic grouping (2).

Further specific examples of esters of pyroglutamic acid which are particularly suited to use as penetration enhancers are:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate 12-hydroxystearyl-2-[pyroglutamoyloxy]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

It is to be understood that the above lists of specific examples of esters of pyroglutamic acid are not exhaustive, there being many other examples expressed by the generic structure of these esters.

Further examples of penetration enhancers include:
Dimethyl sulphoxide
N,N-Dimethyl acetamide
N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
Diethyl-m-toluamide, and
1-Dodecylazacyloheptan-2-one Further examples of penetration enhancers include wetting agents, by which term is meant a surface active agent which, when added to water, causes it to penetrate more easily into, or spread on the surface of another material, by reducing the surface tension of water at the water-air interface; [The Condensed Chemical Dictionary, Eighth Edition 1971, pg 937].

By "surface active agent" is meant, any compound that reduces surface tension when dissolved in water or water solutions; [The Condensed Chemical Dictionary, Eighth Edition 1971, pg 840].

By "surface tension", is meant the inward force of the liquid, due to the attraction of the molecules below the surface. This force varies from one liquid to another, that of water being high compared with that of alcohol, for example; [The Condensed Chemical Dictionary, Eighth Edition 1971 pg 841].

The function of the wetting agent in the composition according to the invention is accordingly to enable the culture supernatant to be dispersed readily on the skin's surface or on the hair, and to facilitate its penetration into the skin to the region of the hair bulb and the associated dermal papilla cells.

The selection of a wetting agent for this purpose presents a wide range of possibilities known in the art.

Particularly preferred examples of wetting agents include the following surface active agents.

(i) Anionic surface active agents, such as metallic or alkanolamine salts of fatty acids for example sodium laurate and triethanolamine oleate;
alkyl benzene sulphones, for example triethanolamine dodecyl benzene sulphonate;
alkyl sulphates, for example sodium lauryl sulphate;
alkyl ether sulphates, for example sodium lauryl ether sulphate [2 to 8 EO];
sulphosuccinates, for example sodium dioctyl sulphonsuccinate;
monoglyceride sulphates, for example sodium glyceryl monostrearate monosulphate;
isethionates, for example sodium isethionate;
methyl taurides, for example Igepon T;
acylsarcosinates, for example sodium myristyl sarcosinate;
acyl peptides, for example Maypons and Lamepons;
acyl lactylates,
polyalkoxylated ether glycollates, for example trideceth-7 carboxylic acid;
phosphates, for example sodium dilauryl phosphate.

(ii) Cationic surface active agents, such as amine salts, for example sapamin hydrochloride;
quartenary ammonium salts, for example Quaternium 5, Quaternium 31 and Quaternium 18;

(iii) Amphoteric surface active agents, such as imidazol compounds, for example Miranol;
N-alkyl amino acids, such as sodium cocaminopropionate and asparagine derivatives;
betaines, for example cocamidopropylebetaine (iv) Nonionic surface active agents, such as fatty acid alkanolamides, for example oleic ethanolamide;
esters of polyalcohols, for example Span; polyglycerol esters, for example that esterified with $C_{12-18}$ fatty acids and one or serveral OH groups;
polyalkoxylated derivatives, for example polyoxy:-polyoxyethylene stearate;
ethers, for example polyoxyethe lauryl ether;
ester ethers, for example Tween;
amine oxides, for example coconut and dodecyl dimethyl amine oxides.

Mixtures of two or more of the above surface active agents can be employed as wetting agents in the composition according to the invention.

The amount of activity enhancer, when employed in accordance with the invention, will normally be from 0.1 to 50%, preferably from 0.5 to 25% and most preferably from 0.5 to 10% by weight of the composition.

Other ingredients

The composition according to the invention can contain ingredients other than those already mentioned, depending on the form of the intended product. It is, for example, possible to include antiseptics, preservatives, antioxidants, emulsifiers, colouring agents and detergents.

The composition according to the invention can also be employed as a vehicle for a wide variety of cosmetically or pharmaceutically active ingredients, particularly ingredients which have some beneficial effect when applied to the skin other than the promotion of hair growth.

Process

The invention also provides a process for the preparation of a composition suitable for topical application to the hair and/or scalp which comprises the step of concentrating the cell-free supernatant from cultured dermal papilla cells.

Product Form

The compositions of the invention can be formulated as liquids, for example as a lotion, shampoo, conditioner or milk for use in conjunction with an applicator such as a roll-ball applicator, or a spray device such as an aerosol can containing propellant, or a container fitted with a pump to dispense the liquid product. Alternatively, the compositions of the invention can be solid or semisolid, for example sticks, creams or gels, for use in conjunction with a suitable applicator or simply a tube, bottle or lidder jar, or as a liquid-impregnated fabric, such as a tissue wipe.

The invention accordingly also provides a closed container containing a composition as herein defined.

Use of Compositions to Induce, Maintain or Increase Hair Growth

The invention also provides for the use of the concentrated cell-free supernatant obtained from cultured dermal papilla cells, preferably hair growth promoter derived therefrom, in the topical treatment of baldness.

The compositions according to the invention are primarily intended for topical application to the scalp of the human subject, to increase hair growth particularly where the head is already bald or balding. The compositions can also be applied profilactically to the hair and to the scalp to reduce or prevent the onset of baldness.

The amount of the composition and the frequency of application to the hair and/or scalp can vary widely, depending on personal needs, but it is suggested as an example that topical application of from 1 to 5g daily containing from 0.000001 to 1g of the hair growth promoter over the period of at least six months will in most cases result in an improvement in hair growth.

THE BIOSYNTHESIS AND ISOLATION OF THE HAIR GROWTH PROMOTER

The invention also provides a process for the preparation of a hair growth promoter, which comprises the step of:

(i) inoculating a nutrient medium with dermal papilla fibroblasts,
(ii) incubating with the medium at a temperature of from 15° to 45,
(iii) separating the supernatant from the culture,
(iv) concentrating the cell-free supernatant at least 50 times, the concentrate so obtained containing a proteinaceous hair growth promoter which is characterised by:

(a) having an apparent molecular weight of at least 500D; and
(b) possessing the ability to initiate DNA synthesis of serum-starved NIH 3T3 cells.

A preferred method for the biosynthesis and subsequent isolation of the hair growth promoter can be carried out as follows:

1. Dissection of dermal papillae from hair follicles and culture of human dermal papilla cells Dermal papillae were isolated by microdissection from hair follicles.

The isolated papillae were maintained in a medium containing 15% by volume fetal calf serum (FCS), the cells and medium being kept at 37° C. in an atmosphere of 5% $CO_2$/95% air, in order to maintain a suitable pH value of from 6.5 to 7.5.

The medium employed was Dulbeccos' modified Eagles medium (DMEM) supplemented with L-glutamine, 15% by volume FCS, as well as penicillin and streptomycin to reduce the risk of bacterial contamination.

Following attachment of the dermal papillae to the culture vessel, cells migrating from dissected papillae were allowed to grow to confluence in the above nutrient medium before being 'passaged' into fresh medium to allow expansion of cell numbers. Passaging was achieved by washing the cells in phosphate buffered saline (PBS), addition of warmed trypsin/EDTA solution (37° C.) for about 5 minutes, detachment of rounded cells and 'splitting' the harvested cells into new culture vessels containing medium with fresh serum. In the presence of serum, most cells reattach and spread rapidly on the surfaces of the culture vessels. Nutrient medium containing serum was changed routinely twice per week, and by this means dermal papilla fibroblasts were grown continously, so providing a continous supply of cells and culture supernatant containing the hair growth promoter.

2. Collection of culture supernatant

After a period of at least 3 days, the culture supernatant was decanted from the cells and centrifuged to remove floating cells and cell debris, and then concentrated and dialysed against isotonic saline using, for example, an Amicon ultra-filtration device having a 500D, 2000D or 500DD (D=Dalton) molecular weight cut off. Fresh medium was added to the dermal papilla cells so that with time further culture supernatant could be obtained.

The concentrated, dialysed culture supernatant containing the hair growth promoter can then be used as such in preparing the composition according to the invention, or it can be dried, for example, by freeze drying before dispersing in the vehicle.

3. Assay of culture supernatant from human dermal papilla fibroblasts

In order to assay the molecules made by dermal papilla fibroblasts and exported into the medium for their ability to promote hair growth, it is necessary to maintain the cells in serum-free medium (SFM). This is achieved by washing the cells twice with PBS and placing them in SFM for 24 hours. This medium is then discarded as it contains traces of serum and replaced with fresh SFM. After three days, this medium is poured off and is centrifuged, concentrated and dialysed as described above.

There are several biological assays which an be used to assess potential hair growth activity present in the concentrated serum-free culture supernatant. A preferred assay is a mitogenisis assay, which assesses the ability of the concentrated culture supernatant to stimulate DNA synthesis in a test cell line (NIH-3T3).

According to this assay, test cells are rendered quiescent in low serum medium (DMEM +L-glutamine +0.5 to 0.7 FCS) for 24 to 48 hours, and the ability of stimulants, (that is in this case concentrated culture supernatant) to increase the uptake of tritiated thymidine into DNA Material over a 24 hour period, is assessed.

4. Interpretation of results

The concentrated culture supernatant shows an activity in terms of its ability to initiate DNA synthesis as mentioned by the uptake of tritiated thymidine into DNA, otherwise known as mitogenic activity. As the dermal papilla cells in vivo regulate the mitogenic activity of epithelial cells in the hair bulb, this activity of the concentrate is therefore in part related to its ability to stimulate hair growth on application to skin.

The hair growth promoter responsible for this DNA synthesis in NIH-3T3 cells has been shown to have a molecular weight of at least 500D. Using the NIH-3T3 cells DNA synthesis assay the concentrated cell culture supernatant has the following properties. It is unstable to heating in aqueous solution for 1 minute at 100° C.

but stable to heating for ten minutes at 60° C. The mitogenic activity is promoted in the presence of insulin or insulin-like growth factor 1 (IGF1), but not by the presence of epidermal growth factor((EGF). The activity is partially stable to lowering of the pH in 0.1M acetic acid or 0.1% trifluoroacetic acid (TFA) and readjustment of this pH to 7.0, and is partially stable to the process of freeze drying or to repeated freeze-thaw cycles of the concentrated cell culture supernatant. Fractionation studies show that the cell culture supernatant contains a number of separate components able to promote DNA synthesis in NIH-3T3 cells.

EVALUATION OF EFFICACY OF HAIR GROWTH STIMULANTS USING THE RAT MODEL (i) Measurement of hair growth using the rat model The effect of compounds on hair growth was assessed using male rats as an animal model as follows. In each of the comparisons reported below, 10 rats were used.

A small patch of normal skin (4 cm×4 cm) on the upper back of each rat was clipped at the start and a hair growth stimulant composition (or a control) applied twice daily topically or continuously subcutaneously to the clipped area. Hair was clipped from the area of the patch twice weekly, collected and weighed at each time point, and cumulative hair weight calculated. From these data, it was possible to estimate the effect of a hair growth stimulant as a test compound on the amount and duration of hair growth during the experiment. A positive response, i.e. an increase of at least 10% by weight of hair, compared with a control indicates the potential of the test substance to prevent hair loss and/or reverse baldness in human subjects.

(ii) Validation of rat model for hair growth using Minoxidil

The rat model was validated by showing that topical application of a known promoter of human hair regrowth, namely 2% (w/v) minoxidil in a vehicle of 70% ethanol, 20% water and 10% propylene glycol, caused an increase of 55% in hair growth as shown below in Table 1:

TABLE 1

| Treatment | Mean Cumulative Hair weight (mg) after 45 days |
| --- | --- |
| 2% minoxidil | 599.2 |
| Vehicle (control) | 387.3 |

In vivo assay of rat cell-free concentrated culture supernatant

A hair growth promoter concentrate was prepared as described hereinbefore. This concentrate was derived from cultured rat dermal papilla fibroblasts (passages 1 and 2), the cell-free supernatant being concentrated approximately 100 times and dialysed into phosphate buffered saline using a protein filter having a molecular weight cut off approximately 0000 Daltons. In these experiments, rat (as opposed to human) culture supernatant was used to avoid potential problems due to species variation.

In the test experiment, the cell-free supernatant concentrate was assayed in an in vivo rat hair growth model. It was delivered continuously (about 0.5 microliters per hour) to the animal over a three week period using a mini osmotic pump (model 2002) commercially available from Alza, USA. In setting up the experiment, a 4×4 cm square area of skin was clipped free of hair on the upper back of male rats just below the shoulders. The mini osmotic pumps were assembled according to the manufacturer's instructions and implanted singly subcutaneously just behind the posterior edge of the clipped site. A short 1.3 cm canular was attached to the pump so that the contents of the pump could be delivered accurately under the clipped site. It was considered that subcutaneous delivery of the concentrate was equivalent in its effect on hair growth to topical application of it, while simplifying accurate dosing to the site of application.

The effect of the concentrated culture supernatant was assessed by comparing the cumulative weight of hair produced in the test and control samples.

In control experiments, the pumps were filled with PBS. A total of 240 microliters [approximately] of sample was delivered to each rat. Ten animals were used for the control sample, and ten for the test sample, each animal being 65 days old at the beginning of the experiment, at which point the hair follicles are in anagen midway through the G3 growth phase.

| | CUMULATIVE HAIR GROWTH (mg) | | | |
| --- | --- | --- | --- | --- |
| DAYS | TEST MEANS | CONTROL MEANS | TEST MINUS CONTROL | % INCREASE OVER CONTROL |
| 2 | 39.60 | 35.80 | 3.8 | 10.6 |
| 6 | 86.40 | 61.70 | 24.7 | 40.0 |
| 9 | 127.10 | 104.30 | 22.8 | 21.9 |
| 13 | 166.90 | 146.80 | 20.1 | 13.7 |
| 16 | 207.00 | 175.00 | 32.0 | 18.3 |
| 20 | 264.00 | 212.30 | 52.1 | 24.5 |

The effect of the cell-free supernatant concentrate was to stimulate an increased in hair growth as measured by the weight of hair produced.

EXAMPLES

The invention is illustrated by the following examples. In each case, the hair growth promoter ingredient is a culture supernatant which has been concentrated and dialysed, as described herein, and contains 3mg/ml protein.

EXAMPLE 1

This Example illustrates a lotion according to the invention which is suitable for topical application to the scalp in order to promote hair growth.

The lotion has the following formulation:

| | % w/w |
| --- | --- |
| Hair growth promoter | 1 |
| water | 97 |
| preservative | 2 |
| perfume | q.s. |

This Example illustrates a hair tonic which is suitable for application to hair or scalp.

The hair tonic has the following formulation:

| | % w/w |
| --- | --- |
| Hair growth promoter | 0.1 |
| ethanol | 13 |
| water | 86.9 |

-continued

|  | % w/w |
|---|---|
| perfume | q.s. |

This Example also illustrates a lotion which is suitable for topical application to the scalp.
The lotion has the following formulation:

|  | % w/w |
|---|---|
| Hair growth promoter | 15 |
| propan-2-ol | 10 |
| ethanol | 15 |
| perfume | q.s. |
| Water | 60 |

EXAMPLE 4

This example also illustrates a hair tonic which is suitable for application to hair or scalp.
The hair tonic has the following formulation:

|  | % w/w |
|---|---|
| Hair growth promoter | 20 |
| ethanol | 20 |
| water | 60 |
| perfume | q.s. |

EXAMPLES 5 to 8

The following formulations represent lotions which can be used topically in the treatment of bald or balding male or female heads.

|  | % w/w | | | |
|---|---|---|---|---|
|  | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| Hair growth promoter | 25 | 10 | 8 | 1 |
| Perfume | 1 | 1 | 1 | 1 |
| Water | to 100 | 100 | 100 | 100 |

EXAMPLE 9

This Example illustrates water-in-oil high internal phase emulsion containing a hair growth promoter according to the invention.
The emulsion consisted of 10% by volume oily phase and 90% by weight aqueous phase.
The oily phase and the aqueous phase had the following consitution:

|  | % w/w |
|---|---|
| Oily phase | |
| Sorbitan monooleate | 20 |
| Quartenium-18 hectorite | 5 |
| Liquid paraffin | 75 |
| Aqueous phase | |
| Hair growth promoter | 15 |
| Xanthan gum | 1 |
| Preservative | 0.3 |
| Perfume | q.s. |
| Sodium chloride (1% w/w solution) | to 100 |

The emulsion was prepared by taking 10 parts by volume of the oily phase and to it adding slowly with stirring 90 parts by volume of the aqueous phase.
The high internal phase water-in-oil emulsion so formed can be applied topically to the scalp, to improve hair growth and regrowth.
The following examples 10 to 12 illustrate shampoos for use in washing the hair and scalp, and for promoting hair growth on the scalp.

EXAMPLE 10

|  | % w/w |
|---|---|
| Sodium lauryl ether sulphate (2 EO): 21% AD | 41.4 |
| Lauryl dimethylamino acetic acid betaine: 30% AD | 4 |
| Coconut fatty acid diethanolamine | 1.5 |
| Oleyl triethoxy phosphate (BRIPHOS 03D) | 1 |
| Polyglycol-polyamine condensation resin (POLYQUART H): 50% active | 1.5 |
| Preservative, colouring matter, salt | 0.58 |
| Hair growth promoter | 15 |
| Perfume | q.s. |
| Water | to 100 |

EXAMPLE 11

|  | % w/w |
|---|---|
| Sodium lauryl ether sulphate (2 EO): 100% AD | 12 |
| POLYQUART H: 50% active | 2.5 |
| BRIPHOS 03D | 2.5 |
| Hair growth promoter | 24 |
| Zinc Sulphate | 5 |
| Perfume | q.s. |
| Water | to 100 |

EXAMPLE 12

|  | % w/w |
|---|---|
| Monoethanolamine lauryl sulphate: 100% AD | 20 |
| POLYQUART H: 50% active | 3 |
| BRIPHOS 03D | 1.7 |
| Coconut diethanolamide | 5 |
| Hair growth promoter | 25 |
| Perfume | q.s. |
| Water | to 100 |
| pH adjusted to 6.5 | |

EXAMPLES 13 to 24

These examples illustrate lotions according to the invention, each containing an activity enhancer which can be used topically in the treatment of bald or balding male or female heads, in order to initiate or promote or enhance hair growth.

|  | % w/w | | |
|---|---|---|---|
| Example No. | 13 | 14 | 15 |
| Minoxidil | 1 | 2 | 5 |
| Absolute ethanol | 10 | 20 | 30 |
| Hair growth promoter | 10 | 5 | 1 |
| Paramethyl benzoate | 0.2 | 0.2 | 0.2 |
| Perfume | q.s. | q.s. | q.s. |
| Water | to 100 | to 100 | to 100 |
| Example No. | 16 | 17 | 18 |

-continued

|  | % w/w | | |
|---|---|---|---|
| Esterified disaccharide* | 1 | 2 | 5 |
| Absolute ethanol | 10 | 15 | 20 |
| Hair growth promoter | 15 | 5 | 1 |
| Paramethyl benzoate | 0.2 | 0.2 | 0.2 |
| Perfume | q.s. | q.s. | q.s. |
| Hydroxethyl cellulose | — | 0.4 | — |
| Water | to 100 | to 100 | to 100 |

| Example No. | 19 | 20 | 21 |
|---|---|---|---|
| Zinc sulphate | 1 | 5 | 10 |
| Absolute ethanol | 5 | — | — |
| Hair Growth Promoter | 10 | 5 | 1 |
| Perfume | q.s. | q.s. | q.s. |
| Paramethyl benzoate | — | 0.2 | 0.2 |
| Water | to 100 | to 100 | to 100 |

| Example No. | 22 | 23 | 24 |
|---|---|---|---|
| N—methyl pyrrolidone | 1 | 5 | 10 |
| Absolute ethanol | — | — | 5 |
| Hair growth promoter | 10 | 5 | 0.5 |
| Hydroxyethyl cellulose | 0.4 | 0.4 | 0.4 |
| Paramethyl benzoate | 0.2 | 0.2 | 0.2 |
| Perfume | q.s. | q.s. | q.s. |
| Water | to 100 | to 100 | to 100 |

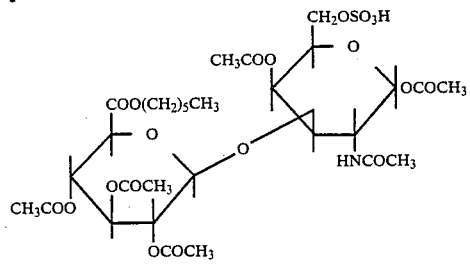

I claim:

1. A composition suitable for topical application to mammalian skin or hair, comprising an amount of a concentrated cell-free supernatant from a culture of dermal papilla fibroblasts which is sufficient to increase hair growth in the rat, when applied thereto, by at least 10% more than that obtainable using a control composition from which the said cell-free supernatant has been omitted.

2. The composition of claim 1, wherein the supernatant has been concentrated at least 50 times.

3. The composition of claim 1, wherein the supernatant has been concentrated at least 100 times.

4. The composition of claim 1, wherein the supernatant comprises a proteinaceous hair growth promoter which is characterised by:
   (i) having an apparent molecular weight of at least 500D; and
   (ii) possessing the ability to initiate DNA synthesis in a culture of serum-starved NIH 3T3 cells.

5. The composition of claim 4, wherein the hair growth promoter has an apparent molecular weight of from 500D to 1,000,000D.

6. The composition of claim 4, wherein the hair growth promoter has an apparent molecular weight of at least 2000D.

7. The composition of claim 1, wherein the supernatant has a protein level of not greater than 10 mg/ml.

8. The composition of claim 4, wherein the hair growth promoter forms from 0.00001 to 99% by weight.

9. The composition of claim 1, which comprises a cosmetically acceptable vehicle in addition to the culture supernatant.

10. The composition of claim 9, wherein the vehicle forms from 1 to 99.9999% by weight.

11. A composition suitable for topical application to mammalian skin or hair comprising:
   (i) an amount of a hair growth promoter, or active fragments thereof, sufficient to increase hair growth in the rat, when applied thereto, by at least 10% more than that obtainable using a control composition from which the said hair growth promoter has been omitted; and
   (ii) a cosmetically acceptable vehicle,
   the hair growth promoter having been obtained from a concentrated cell-free supernatant of cultured dermal papilla fibroblasts, the hair growth promoter being proteinaceous, and being further characterised by:
   (a) having an apparent molecular weight of at least 500D; and
   (b) possessing the ability to initiate DNA synthesis in a culture of serum starved NIH 3T3 cells.

12. A composition suitable for topical application to mammalian skin or hair comprising:
   (i) an amount of hair growth promoter, or active fragments thereof, sufficient to increase hair growth in the rat, when applied topically thereto by at least 10% more than that obtainable using a control composition from which the said hair growth promoter has been omitted; and
   (ii) a cosmetically acceptable vehicle,
   the hair growth promoter having been obtained from a cell-free supernatant of cultured dermal papilla fibroblasts following:
   inoculation of a nutrient medium with dermal papilla fibroblasts;
   incubation at a temperature of from 15° to 45° C. for at least 24 hours
   separation of the supernatant liquor from the culture; and
   concentration of said supernatant liquor at least 50 times;
   the hair growth factor so obtained being characterised by:
   (a) having a molecular weight of at least 500 D; and
   (b) possessing the ability to at least double the synthesis of DNA in serum starved 3T3 cells as measured by uptake of tritiated thymidine.

13. The composition of claim 1, which additionally comprises an activity enhancer chosen from other hair growth stimulants, protein stabilising agents and penetration enhancers.

14. The composition of claim 13, wherein the other hair growth stimulant is chosen from minoxidil, minoxidil glucuronides, minoxidil sulphates or mixtures thereof.

15. The composition of claim 13, wherein the protein stabilising agent is chosen from glycerol, ethylenediaminetetraacetic acid, cysteine, $\alpha_2$-macroglobulin, serum or mixtures thereof.

16. The composition of claim 13, wherein the penetration enhancer is chosen from diisopropyl sebacate, $C_1$ to $C_{30}$ alkyl esters of pyroglutamic acid, 2-pyrrolidone, 1-methyl-2-pyrrolidone or mixtures thereof.

17. A process for the preparation of a hair growth promoter, which comprises the steps of:
   (i) inoculating a nutrient medium with dermal papilla fibroblasts,
   (ii) incubating with the medium at a temperature of from 15° to 45° C., (iii) separating the supernatant from the culture, and (iv) concentrating the cell-free supernatant at least 50 times, the concentrate so obtained containing a proteinaceous hair growth promoter which is characterised by:

(a) having an apparent molecular weight of at least 500D; and (b) possessing the ability to initiate DNA synthesis of serum-starved NIH 3T3 cells.

* * * * *